US008993267B2

(12) United States Patent
Bodie et al.

(10) Patent No.: US 8,993,267 B2
(45) Date of Patent: Mar. 31, 2015

(54) CONDITIONING BIOMASS FOR MICROBIAL GROWTH

(75) Inventors: Elizabeth A Bodie, San Carlos, CA (US); George England, Redwood City, CA (US)

(73) Assignee: Danisco US Inc., Palo Alto, CA (US)

( * ) Notice: Subject to any disclaimer, the term of this patent is extended or adjusted under 35 U.S.C. 154(b) by 743 days.

(21) Appl. No.: 12/521,786

(22) PCT Filed: Dec. 17, 2007

(86) PCT No.: PCT/US2007/025911
§ 371 (c)(1),
(2), (4) Date: Sep. 2, 2009

(87) PCT Pub. No.: WO2008/085356
PCT Pub. Date: Jul. 17, 2008

(65) Prior Publication Data
US 2009/0311752 A1 Dec. 17, 2009

Related U.S. Application Data

(60) Provisional application No. 60/878,616, filed on Jan. 3, 2007.

(51) Int. Cl.
*C12P 21/04* (2006.01)
*C12N 1/22* (2006.01)
*C12N 1/38* (2006.01)
*C12N 9/02* (2006.01)
*C12N 9/42* (2006.01)

(52) U.S. Cl.
CPC .. *C12N 1/22* (2013.01); *C12N 1/38* (2013.01); *C12N 9/001* (2013.01); *C12N 9/0059* (2013.01); *C12N 9/0061* (2013.01); *C12N 9/0071* (2013.01); *C12N 9/2437* (2013.01)
USPC ........................ 435/71.1; 435/252; 435/254.6

(58) Field of Classification Search
USPC .............................. 435/71.1, 252, 254, 254.6
See application file for complete search history.

(56) References Cited

U.S. PATENT DOCUMENTS

| | | | | |
|---|---|---|---|---|
| 4,569,915 | A * | 2/1986 | Ring | ........................ 435/254.1 |
| 6,168,936 | B1 * | 1/2001 | Wang | ............................ 435/189 |
| 6,426,410 | B1 | 7/2002 | Wang | |
| 6,475,566 | B1 | 11/2002 | Messner et al. | |
| 6,905,853 | B1 | 6/2005 | Wang | |
| 7,067,303 | B1 | 6/2006 | Nichols et al. | |

OTHER PUBLICATIONS

Mahmood et al. Biotechnol. Lett. (1985) 7(3): 207-212.*
Bigelow et al. Appl. Biochem. Biotechnol. (2002) 98-100: 921-934.*
Jonsson et al. Appl. Microbiol. Biotechnol. (1998) 49: 691-697.*
Larrson et al. Appl. Biotechnol. Biotechnol. (1999) 77-79: 91-103.*
Holker et al. Folia Microbiol. (2002) 47(4): 423-427.*
Higuchi, T. Proc. Japan Academy, Ser. B (2004) 80: 204-214.*
Mander et al. Appl. Environ. Microbiol. (Jul. 2006) 72(7): 5020-5026.*
Iimura et al. Tokyo Noko Daigaku Nogakubu Enshurin Hokoku (1991) 28: 65-69 (abstract only).*
Web page from http://earthmedicineinstitute.com/more/library/medicinal-plants/trametes-versicolor/ downloaded May 4, 2014.*
Breccia et al. Acta Biotechnol. (1997) 17(2): 177-184.*
Viridiana et al. (PLOS ONE (2013) 8(1): e55295, pp. 1-17.*
Iimura et al. Biosci. Biotech. Biochem. (1995) 59(5): 903-905.*
Bauer, R. et al. "Use of syringaldazine in a photometric method for estimating "free" chlorine in water." *Analytical Chemistry* 43(3): 421-425, Mar. 1, 1971.
Childs, R.E. et al. "The steady-state kinetics of peroxidase with 2,2'-azino-di-(3-ethyl-benzthiazoline-6-sulphonic acid) as chromogen.." *Biochemical Journal* 145(1): 93-103, Jan. 1975.
Cunningham, B.C. et al. "High-resolution epitope mapping of hGH-receptor interactions by alanine-scanning mutagenesis." *Science* 244(4908): 1081-1085, Jun. 2, 1989.
Doppelbauer, R. et al. "The use of lignocellulosic wastes for production of cellulase by *Trichoderma reesei*." *Applied Microbiology and Biotechnology* 26(5): 485-494, 1987.
Haars, A. et al. "Effect of phenolic compounds and tannin on growth and laccase activity of Fomes annosus." *European Journal of Forest Pathology* 11(1-2): 67-76, 1981.
Lin, Y. et al. "Ethanol fermentation from biomass resources: current state and prospects." *Applied Microbiology and Biotechnology* 69(6): 627-642, Feb. 1, 2006.
Mander, et al., "Use of Laccase as a Novel, Versatile Reporter System in Filamentous Fungi," *Applied and Environmental Microbiology*, vol. 72, No. 7, pp. 5020-5026, 2006.
Martin, et al, "Ethanol Production from Enzymatic Hydrolysates of sugarcane Bagasse using Recombinant Xylose-utilising *Saccharomyces cerevisiae*," Enzyme and Microbial Technology, vol. 31, pp. 274-282, 2002.
Mussatto, S.I. et al. "Alternatives for detoxification of diluted-acid lignocellulosic hydrolyzates for use in fermentative processes: a review." *Bioresource Technology* 93(1): 1-10, May 2004.
Needleman, S.B. et al. "A general method applicable to the search for similarities in the amino acid sequence of two proteins." *J. Mol. Biol* 48(3): 443-53, Mar. 1970.

(Continued)

*Primary Examiner* — Susan Hanley
(74) *Attorney, Agent, or Firm* — Danisco US Inc.

(57) ABSTRACT

The present invention relates to methods for improving the yield of microbial processes that use lignocellulose biomass as a nutrient source. The methods comprise conditioning a composition comprising lignocellulose biomass with an enzyme composition that comprises a phenol oxidizing enzyme. The conditioned composition can support a higher rate of growth of microorganisms in a process. In one embodiment, a laccase composition is used to condition lignocellulose biomass derived from non-woody plants, such as corn and sugar cane. The invention also encompasses methods for culturing microorganisms that are sensitive to inhibitory compounds in lignocellulose biomass. The invention further provides methods of making a product by culturing the production microorganisms in conditioned lignocellulose biomass.

8 Claims, 1 Drawing Sheet

(56) References Cited

OTHER PUBLICATIONS

Nilvebrant, N.-O. et al. "Limits for alkaline detoxification of dilute-acid lignocellulose hydrolysates." *Applied Biochemistry and Biotechnology* 107(1): 615-628, Mar. 1, 2003.

Palmqvist, E. et al. "Fermentation of lignocellulosic hydrolysates. I: inhibition and detoxification." *Bioresource Technology* 74(1): 17-24, Aug. 2000.

Palmqvist, E. et al. "Fermentation of lignocellulosic hydrolysates. II: inhibitors and mechanisms of inhibition." *Bioresource Technology* 74(1): 25-33, Aug. 2000.

Pearson, W.R. et al. "Improved Tools for Biological Sequence Comparison." *Proc. Natl. Acad. Sci.* USA 85(8): 2444-2448, Apr. 15, 1988.

Persson, P. et al. "Effect of Different Forms of Alkali Treatment on Specific Fermentation Inhibitors and on the Fermentability of Lignocellulose Hydrolysates for Production of Fuel Ethanol." *Journal of Agricultural and Food Chemistry* 50(19): 5318-5325, 2002.

Rifai, M.A. "Trichoderm *piluliferum*." In a revision of the genus *Trichoderma*, pp. 16-18. Mycological Papers 116. Surrey, England: Commonwealth Mycological Institute, 1969.

Saha, B. "Hemicellulose bioconversion." *Journal of Industrial Microbiology and Biotechnology* 30(5): 279-291, May 24, 2003.

Setti, L. et al. "Laccase catalyzed-oxidative coupling of 3-methyl 2-benzothiazolinone hydrazone and methoxyphenols." *Enzyme and Microbial Technology* 25(3-5): 285-289, Aug. 1999.

Sheir-Neiss, G. et al. "Characterization of the secreted cellulases of *Trichoderma reesei* wild type and mutants during controlled fermentations." Applied Microbiology and Biotechnology 20(1): 46-53, Jul. 1, 1984.

Smith, T.F. et al. "Comparison of biosequences." Adv. Appl. Math 2: 482-489, 1981.

International Search Report for PCT/US07/025911, 2 pp., mailed Jun. 4, 2008.

\* cited by examiner

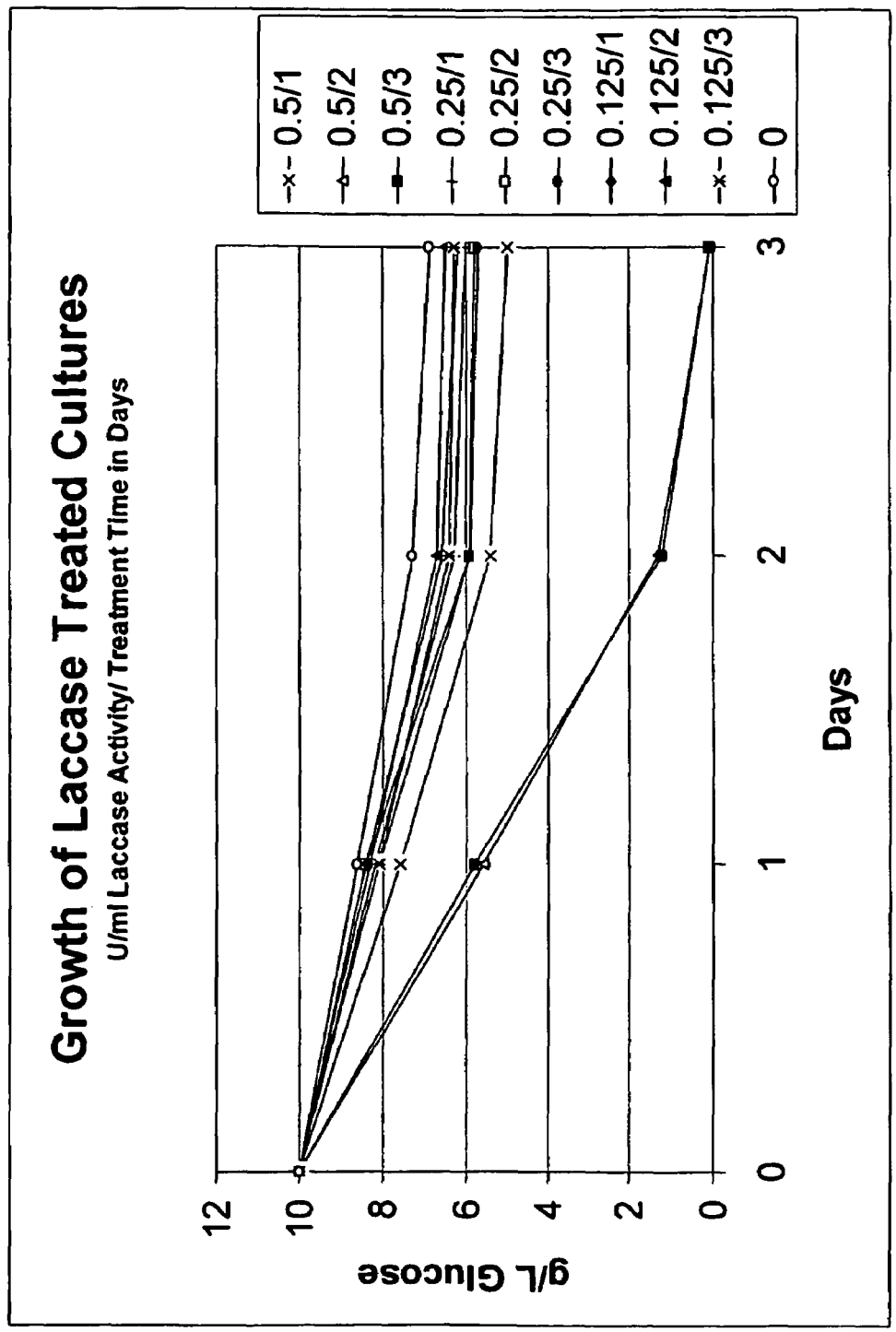

US 8,993,267 B2

CONDITIONING BIOMASS FOR MICROBIAL GROWTH

1. CROSS-REFERENCES TO RELATED APPLICATION

The present application claims benefit of and priority to U.S. Provisional Application Ser. No. 60/878,616, entitled "Conditioning Biomass for Microbial Growth", filed Jan. 3, 2007, incorporated herein by reference in its entirety.

GOVERNMENT SUPPORT

Portions of this work were funded by Subcontract No. ZCO-30017-01 with the National Renewable Energy Laboratory under Prime Contract No. DE-AC36-99GO10337 with the U.S. Department of Energy. Accordingly, the United States Government may have certain rights in this invention.

2. INTRODUCTION

The invention relates to a method for improving the yield of microbial processes that uses lignocellulose biomass as a nutrient source.

3. BACKGROUND OF THE INVENTION

In recent years, considerable advances have been made in the conversion of biomass into ethanol as fuel. Most of the ethanol produced from biomass up to now is based on fermentation of corn glucose in the United States and sugarcane sucrose in Brazil. Biomass which largely consists of cellulose, hemicellulose and lignin has attracted increasing attention as an important renewable source of energy. Forestry and agricultural residues are abundant and relatively inexpensive. If this material, or at least a significant part of it, could be converted into liquid fuel, this would constitute a significant contribution to solving the problem of recycling and conservation of resources.

Ethanol can be produced from lignocellulose materials, such as wood and crop residues. The cellulose and hemicellulose components of lignocellulose can be hydrolyzed to release monosaccharides which are then fermented to ethanol. However, it has been difficult to develop an economically viable process of converting cellulosic material into fermentable sugars. The research in using lignocellulose biomass for making ethanol and other products is widely reviewed, see for example Lin and Tanaka (2006 Appl. Microbiol. Biotechnol. 69:627-642) and Saha (2003, J. Ind. Microbiol. Biotechnol. 30:279-291).

Lignocellulose is a more complex substrate than starch and sugars. One of the rate-limiting and difficult tasks is the removal of lignin. Moreover, plant tissues differ tremendously with respect to size and organization. Some plant cell types have thick cell walls and a highly lignified middle lamella separating cells from one another. These cell walls must be attacked from the luminal surface out through the secondary wall (as opposed to particles of pure cellulose, which are degraded from the outside inward). In addition to constraints imposed by the structure of cellulose itself, further limitations are imposed by diffusion and transport of the cellulolytic agent to the site of attack. Thus, prior to hydrolysis of cellulose, most woody materials are subjected to a pretreatment to make the cellulose fibers within the structures more amenable and accessible to hydrolysis.

It has been observed that fermentation of wood-derived hydrolysates to ethanol is made difficult by the presence of inhibitory substances, such as furans, organic acid and various phenolic compounds. Such inhibitory compounds are formed or released during lignin degradation and hydrolysis of complex polysaccharides in wood. The kind of toxic compounds and their concentration in lignocellulose hydrolysates depend on both the raw material and the operational conditions employed for hydrolysis. Such toxic compounds can reduce significantly the efficient utilization of sugars and production of ethanol.

A number of biological, physical, and chemical detoxification methods have been tested with hydrolysates of spruce biomass (Larsson et al., 1999, Appl. Biochem. Biotechnol. 77-79, 91-103). U.S. Pat. No. 7,067,303 discloses the use of the fungus Coniochaeta ligniaria to deplete furans in hydrolysates. One commonly used method known as "overliming" involves adjusting the pH initially to 10-11 with an alkali, e.g., calcium hydroxide or ammonia and then to 5.0-6.0 with an acid, e.g., sulfuric or phosphoric acid. The conditions used for detoxification with alkali must be carefully controlled to optimize the positive effects and minimize the degradation of fermentable sugars. The mechanisms behind the alkali detoxification effect and the influence of the choice of cation and conditions are not well understood. (Nilvebrant et al., 2003, Appl Biochem Biotechnol. 105-108:615-28; Persson et al., 2002, J Agric Food Chem. 50(19):5318-25) While overliming is quite effective, it results in an insoluble precipitate that persists through subsequent steps and must be removed and disposed of resulting in waste and increased cost.

The effectiveness of a detoxification method is variable because each type of hydrolysate has a different degree of toxicity, and each species or even strain of microorganism has a different degree of tolerance to inhibitors. Therefore, different detoxification methods cannot be strictly compared when hydrolysates from different sources and different microorganisms are used. (Mussatto and Roberto, 2004, Bioresour Technol. 93(1):1-10; Palmqvist and Hahn-Hagerdal, 2000, Bioresour Technol. 74:25-33; Palmqvist and Hahn-Hagerdal, 2000, Bioresour Technol. 74:17-24). 10010) While the focus of much of the research are directed to detoxifying wood hydrolysates for ethanolic fermentation, the use of lignocellulose biomass as feedstock for other biotechnological processes is relatively unexplored. For example, due to the increased demand for cellulase enzymes in a variety of industries, a need clearly exists for novel methods to increase cellulase production from fungi, e.g., *Trichoderma reesei*, such that cellulase enzymes can be more economically available.

Even within the context of ethanol generation, there is an urgent need for improvement in the economy and efficiency of the various different approaches in converting lignocellulose to sugars to ethanol.

4. SUMMARY OF THE INVENTION

The present invention relates to methods for improving the yield of microbial processes that uses lignocellulose biomass as a nutrient source. In particular, the invention provides methods for preparing a composition comprising lignocellulose biomass that is conditioned for microbial growth. Such a composition can be used as a component in a feedstock for a microbial process. The methods comprise contacting a composition comprising lignocellulose biomass with an enzyme composition that comprises a phenol oxidizing enzyme for a period of time sufficient to neutralize the inhibitory compounds present in the composition. The conditioned composition can support a rate of growth of a species of production microorganism that is higher than that which can be obtained with a lignocellulose biomass composition that was not contacted with the enzyme composition. In one embodiment, the enzyme composition comprises a laccase. In one embodiment, the lignocellulose biomass is derived from non-woody plants, such as corn and/or sugar cane. In one embodiment, the enzyme composition comprises a laccase and the lignocellulose biomass is selected from corn stover and sugar cane bagasse.

The invention also encompasses methods for culturing microorganisms that are sensitive to certain inhibitory compounds present in lignocellulose biomass. In one embodiment, a composition comprising a lignocellulose biomass is contacted with an enzyme composition comprising a phenol oxidizing enzyme for a period of time sufficient to condition the composition for microbial growth. The conditioned composition is then used as a component of the feedstock for culturing the microorganisms. Alternatively, the enzyme composition is added directly to a process wherein the microorganisms are cultured in a culture medium comprising lignocellulose biomass. In either case, the growth rate of the microorganisms and/or the microbial biomass yield in the conditioned composition is increased relative to that of a composition comprising lignocellulose biomass that was not contacted with said enzyme composition.

The invention further encompasses methods for producing a product in a microorganism that uses lignocellulose biomass as a nutrient source. The methods generally involve culturing the microorganisms that produce the product in a composition comprising lignocellulose biomass that is conditioned for microbial growth. The product can be recovered from the microorganisms and/or the conditioned composition. As described above, the composition is conditioned by treatment with a phenol oxidizing enzyme so that the growth rate of the microorganisms obtainable from the conditioned composition is increased relative to that of a composition without conditioning. In certain embodiments, the cultured microorganism is a *Trichoderma* species and the product is a cellulase enzyme.

5. DESCRIPTION OF THE FIGURES

FIG. 1. Growth of laccase-treated cultures. The graph shows the consumption of glucose by a growing culture of *Trichoderma reesei* over a three-day period in a culture medium comprising initially 2% corn stover and 10 g glucose/liter. Glucose concentrations of various cultures that used culture media treated with the indicated concentrations (0 U/ml, 0.125 U/ml, 0.25 U/ml, 0.5 U/ml) of *Trichoderma piluliferum* laccase for the indicated number of days (1, 2, 3 days) are shown by different lines and legend symbols. The control culture was not treated with laccase (0 U/ml).

6. DETAILED DESCRIPTION OF THE INVENTION

The present invention addresses the problem of inhibitory substances in lignocellulose biomass that may adversely affect the performance of microbial cultures that use lignocellulose biomass as a nutrient source. The present invention relates to methods for improving the utility of lignocellulose biomass as a nutrient source for the growth of microorganisms in various types of processes.

The invention involves treating or conditioning a lignocellulose biomass as defined below with an enzyme composition that comprises one or more phenol oxidizing enzymes. Without intending to be bound by any theory or mechanism, some of the inhibitors are phenolic compounds released during the breakdown of lignin and the phenol oxidizing enzymes of the invention are believed to catalyze the oxidative coupling of such phenolic compounds to form insoluble polymeric compounds. The use of phenol oxidizing enzymes in the present invention is distinct from using phenol oxidizing enzymes as a detoxifying agent to aid the breakdown of biomass by other enzymes. The benefit provided by the present invention is improved microbial growth.

After contact with the enzyme composition of the invention, the lignocellulose conditioned for microbial growth can be used directly in a microbial process or subjected to further manipulations. Treatment with the enzyme composition of the invention can alleviate the problems of decreased viability and/or slow growth of production microorganisms and low yield when using lignocellulose biomass as a component of a feedstock. In comparison to overliming, little or no waste is produced when using the invention method.

It is contemplated that the enzyme composition can be used to condition un-pretreated lignocellulose as well as pretreated lignocellulose. As described in detail in Section 6.1, a wide range of untreated lignocellulose can be used in the invention. The enzyme composition of the invention may be used advantageously to reduce the extent of the pretreatment step or even by-pass the pretreatment step. The term lignocellulose biomass includes both untreated and pretreated lignocellulose-containing materials. Pretreated lignocellulose can also be used in the invention. In particular, the invention provides the use of a phenol oxidizing enzyme to condition non-woody lignocellulose biomass, such as corn stover and sugar cane bagasse, or the corresponding hydrolysates, such that the conditioned biomass is more suitable for sustaining the growth of microorganisms. In certain aspects of the invention, the use of purified laccase and purified lignin peroxidase isolated from white-rot fungus (*Trametes versicolor*) to treat wood hydrolysate for ethanolic fermentation is excluded.

The treatment of lignocellulose biomass with the enzyme composition is carried out for a period of time sufficient to decrease the concentration of inhibitory phenolic compounds in the lignocellulose biomass. The treatment can be carried out separately from subsequent process steps. In one embodiment, the treatment of lignocellulose biomass with the enzyme composition can be conducted simultaneously with the growth of production microorganisms. In another embodiment of the invention, the treatment is carried out prior to the introduction of the production microorganisms. In other embodiments, the treatment can be carried out after the lignocellulose has been pretreated. Conditioned lignocellulose biomass and composition comprising the same can be stored for use at a future time. Accordingly, the invention provides methods for preparing a feedstock for culturing microorganisms, wherein a lignocellulose biomass conditioned for microbial growth with an enzyme composition of the invention, is used as a component of a feedstock.

In another embodiment, the enzyme composition can be added directly during culturing of the production microorganisms. The enzyme composition can be added at a time during a process, for example, at the beginning of the process, at a stage when the inhibitory compounds are released, at a stage when the production microorganisms are added to the culture, or at a stage when growth of the production microorganisms is to be maximized. In yet another embodiment, the enzyme composition can be produced by one or more strains of the production microorganism that make the enzyme(s) naturally or recombinantly and secrete the enzyme(s) into the culture.

The enzyme composition comprises at least one phenol oxidizing enzyme. As described in detail in Section 6.2, the phenol oxidizing enzyme can be a laccase produced by a fungus, preferably a filamentous fungus, and most preferably an ascomycete fungus. The phenol oxidizing enzyme can be in various forms, such as but not limited to crystallized form, immobilized form, fungal culture filtrate, and fungal cell extracts.

Use of the enzyme composition improves one or more aspects of the process when it is compared to the same process except the use of lignocellulose that has not been conditioned. For example, the kinetics of microbial growth in a bioreactor or the gain in microbial biomass over unit time at a particular stage of a process can be improved. In various embodiments, the processes contemplated are used for producing a product, such as fuel, commodity chemicals, fine chemicals, enzymes, pharmaceutical intermediates etc. Therefore, the invention also encompasses methods for producing a desired product that involves culturing microorganisms that produce the desired product in conditioned lignocellulose biomass, and recovering the desired product from the process. A detailed description of the types of processes to which the invention can be applied is provided in Section 6.3.

For clarity of disclosure, and not by way of limitation, the detailed description of the invention is divided into the subsections which follow.

6.1 Lignocellulose Biomass

A variety of plant biomass can be used in the present invention. The most abundant plant biomass is lignocellulose in leaves and stalks of woody and non-woody plants. Lignocelluose are composed of heterogeneous intertwined cellulose chains with varying degrees of crystallinity, hemicelluloses and pectins, embedded in lignin. Typically, the cellulose content is in the range of approximately 35% to 50% of plant dry weight and hemicelluloses and lignin, respectively comprise 20% to 35% and 5% to 30% of plant dry weight.

As used herein, the term "woody lignocellulose" refers to lignocellulose present in plants that comprise wood which is the secondary xylem tissue that forms the bulk of the stem and root of a woody plant. Secondary xylem is formed by a vascular cambium and is found in (i) conifers (Coniferae) and (ii) angiosperms (Angiospermae) except monocotyledonous plants. Many conifers are tall trees and the secondary xylem of such trees is known as softwood. Many non-monocot angiosperms are trees, and the secondary xylem of these are known as hardwood. Secondary xylem is also found in members of the gymnosperm groups Gnetophyta and Ginkgophyta and to a lesser extent in members of the Cycadophyta.

Lignocellulose from woody plants would include orchard prunings, chaparral, mill waste (such as bark, chips, shavings, sawdust, and the like), urban wood waste (such as discarded lumber, wood pallets, crates, tree and brush trimmings, etc.), municipal waste (such as newspaper and discarded grocery produce), logging waste and forest thinnings (tree tops, limbs and cull material), short-rotation woody crops such as poplar and cottonwood, and industrial waste (such as wood pulp sludge, waste sulfite liquor from pulp).

The term "non-woody lignocellulose" refers to plant biomass derived from monocotyledonous plants, and especially grassy species belonging to the family Gramineae. Of primary interest are gramineous agricultural residues; that is, the portion of grain-bearing plants that remain after harvesting the seed. Non-woody lignocellulose biomass include without limitation, wheat straw, oat straw, rice straw, barley straw, rye straw, flax straw, sugar cane bagasse, corn stover, corn stalks, corn cobs, corn husks, and the like. Also included within this definition are grasses not conventionally cultivated for agricultural purposes, such as prairie grasses (e.g. big bluestem, little bluestem, Indian grass), switchgrass, gamagrass, and foxtail.

Other agricultural byproducts that are considered plant biomass and contain lignocellulose include waste streams components from commercial processing of crop materials (such as sugar beet pulp, citrus fruit pulp, seed hulls, and the like), cellulosic animal wastes, lawn clippings, and seaweed.

The lignocellulose-containing plant materials can be modified physically, for example, by shredding, crushing, grinding, pulverizing, or macerating. The lignocellulose-containing plant materials can also be soaked in water, soaked in hot water (i.e., above room temperature, e.g., at about 40° C., 50° C., 60° C., 70° C., 80° C., 90° C., 95° C., 99° C., and at normal or above atmospheric pressure), exposed to steam or superheated water, or subject to steam explosion. In an embodiment, the lignocellulose-containing plant material has not been pretreated chemically with acid and/or alkali.

The term "pretreatment" or "chemical pretreatment" are used interchangeably to refer to a process step which converts lignocellulose from its native form, in which it is generally recalcitrant to cellulase action, into a form for which enzymatic hydrolysis is effective and/or efficient. The term "hydrolysate" or variations thereof is used herein to refer to any of the aforementioned lignocellulose that have been pretreated to solubilize at least a portion of the xylan and cellulose in the material and to release sugar monomers. Non-limiting examples of pretreatment include steam explosion in the presence or absence of dilute sulfuric acid or slake lime treatment (i.e., calcium oxide slaked with water to form calcium hydroxide).

The term "lignocellulose" as used herein refers to any of the aforementioned lignocellulose-containing plant materials that has not been chemically pretreated. The term "lignocellulose biomass" refers to any of the aforementioned lignocellulose-containing plant materials in its native form, in a physically modified form (e.g., by shredding or pulverizing), in a water- or steam-treated form, or in a form after chemical pretreatment, that would render it useful as feedstock for growing microorganisms. Woody lignocellulose biomass and non-woody lignocellulose biomass are derived from woody plants and non-woody plants respectively. Typically, lignocellulose biomass is present in a composition, such as a feedstock, as one of several nutrient components.

Among the available agricultural byproducts, corn stover is the most abundant non-woody lignocellulose in the United States. Corn stover comprises the stalk, cob, shuck, and leaves left behind following grain harvest. Collecting the stover can be easily accomplished by turning-off the spreader and/or chopper on the corn combine and picking up the residues by conventional hay baling equipment. Approximately 40% of the dry matter in corn stover is cellulose. Steam pretreatment removes the major part of the hemicellulose from the solid material and makes the cellulose more susceptible to enzymatic digestion. Different combinations of reaction temperature, time, and pH during steam pretreatment can be applied, e.g., 200° C., 5 min, 2% $H_2SO_4$. The liquor following steam explosion can be used for fermentation using *Saccharomyces cerevisiae*. In an embodiment, the corn stover is used in a dry raw form. In other embodiments, corn stover that has been acid-washed and/or water rinsed can also be used.

Another abundant non-woody lignocellulose is sugarcane residues, e.g., bagasse, which is the fibrous residue after sugarcane stalks are crushed to extract their juices. In Brazil, ethanol fuel is produced from sugar cane which is a more efficient source of fermentable carbohydrates than corn. The bagasse has been used as fuel to run the fermentation process.

It is contemplated that sugarcane bagasse and/or its hydrolysates can also be used as a nutrient source for growing microorganisms after it has been conditioned by the methods of the invention. In an embodiment, the sugarcane bagasse is in a dry raw form that has not been pretreated. In other embodiments, the sugarcane bagasse is used in a form that has been acid-washed and/or water rinsed.

Any of the abovementioned lignocellulose biomass can be used in a microbial process directly, or used to make a composition comprising lignocellulose biomass, such as a feedstock. In certain embodiments, lignocellulose biomass which has not been chemically pretreated is preferred as acid or alkali pretreatment generates compounds inhibitory to microbial processes.

6.2 Enzyme Compositions

The present invention provides the use of an enzyme composition that comprises at least one phenol oxidizing enzyme for conditioning a lignocellulose biomass or a composition comprising lignocellulose biomass. The term "phenol oxidizing enzyme" as used herein refers to enzymes that function by catalyzing redox reactions, i.e., the transfer of electrons from an electron donor (usually a phenolic compound) to molecular oxygen (which acts as an electron acceptor) which is reduced to water. Examples of such enzymes are laccases (EC 1.10.3.2), bilirubin oxidases (EC 1.3.3.5), phenol oxidases (EC 1.14.18.1), catechol oxidases (EC 1.10.3.1). The phenol oxidizing enzymes of the present invention are capable of using a wide variety of different phenolic compounds as electron donors, while being very specific for molecular oxygen or hydrogen peroxide as the electron acceptor.

Many phenol oxidizing enzymes exhibit pH optima in the acidic pH range while being inactive in neutral or alkaline pHs. It is preferable to use a phenol oxidizing enzyme whose pH optima falls within the pH range of the lignocellulose biomass. Phenol oxidizing enzymes are known to be produced by a wide variety of fungi, including species of the genera *Aspergillus, Neurospora, Podospora, Botytis, Pleurotus, Trichoderma, Stachybotrys, Fomes, Phlebia, Trametes, Polyporus, Rhizoctonia* and *Lentinus*.

In one embodiment, phenol oxidizing enzymes produced by *Trichoderma* or *Hypocrea* species can be used in the methods of the invention. *Trichoderma* species, strains and natural isolates, and derivatives of such species, strains and isolates, include strains of the species *Trichoderma piluliferum, Trichoderma reesei, Trichoderma longibrachiatum. Trichoderma piluliferum* may be isolated from soil samples, and has been described by J. Webster and Rifai, M. A. 1969, Myco. Pap. 116:16; see also U.S. Pat. No. 6,475,566 (also known as *Hypocrea pilulifera*). In one embodiment, phenol oxidizing enzymes are produced by any fungi that grows on a wood substrate. In one embodiment, any Ascomycetes fungi that make phenol oxidases are used.

The source of a laccase gene for the present invention may be a plant, microbial, insect, or mammalian laccase. In one embodiment, the laccase(s) is a fungal laccase. For example, the laccase(s) may be a filamentous fungal laccase such as a laccase of an *Acremonium, Agaricus, Amerosporium, Antrodiella, Armillaria, Aspergillus, Aureobasidium, Bipolaris, Bjerkandera, Cerrena, Chaetomium, Chrysosporium, Cochliobolus, Coprinus, Cryptococcus, Cryphonectria, Curvularia, Cyathus, Daedalea, Filibasidium, Fomes, Fusarium, Geotrichum, Giocladium, Gongronella, Halosarpheia, Humicola, Hypocrea, Lactarius, Lentinus, Magnaporthe, Monilia, Monocillium, Mucor, Myceliophthora, Neocallimastix, Neurospora, Paecilomyces, Panus, Penicillium, Phanerochaete, Phellinus, Phlebia, Pholiota Piromyces, Pleurotus, Podospora, Pycnoporus, Pyricularia, Rigidoporus, Rhizoctonia, Schizophyllum, Scierotium, Scytalidium sordaria, Sporotrichum, Stagonospora, Talaromyces, Thermoascus, Thielavia, Tolypocladium, Trametes (Polyporus), Vereticiluum, Zalerion, Zythia, Trichoderma* species, or a yeast laccase from *Candida, Kluyveromyces, Pichia, Saccharomyces, Schizosaccharomyces,* or *Yarrowia* species. More specifically, the laccase can be a laccase of *Coprinus cinereus, Myceliophthora thermophila, Trametes villosa (Polyporus pinsitus), Rhizoctonia solani,* or *Scytalidium thermophilum* laccase.

In another embodiment, the laccase(s) is a plant laccase. For example, the laccase(s) may be a lacquer, mango, mung bean, peach, pine, prune, or sycamore laccase. In yet another embodiment, the laccase(s) is an insect laccase. For example, the laccase(s) may be a *Bombyx, Calliphora, Diploptera, Drosophila, Lucilia, Manduca, Musca, Oryctes, Papilio, Phorma, Rhodnius, Sarcophaga, Schistocerca,* or *Tenebrio* laccase.

In yet another embodiment, the laccase(s) is preferably a bacterial laccase. For example, the laccase(s) may be a laccase of *Acer, Acetobacter, Acinetobacter, Actinomyces, Agrobacterium, Alcaligenes, Arthrobacter, Azotobacter, Bacillus, Comamonas, Clostridium, Gluconobacter, Halobacterium, Mycobacterium, Rhizobium, Salmonella, Serratia, Streptomyces, E. coli, Pseudomonas, Wolinella,* or a methylotrophic bacteria. More specifically, the laccase is a *Azospirillum lipoferum* laccase.

In another embodiment, phenol oxidizing enzymes produced by *Stachybotrys* species can be used in the methods of the invention. *Stachybotrys* species, strains and natural isolates, and derivatives of such species, strains and isolates, include strains of the species *Stachybotrys parvispora*, including, in particular, *Stachybotrys parvispora* var. *hughes* MUCL 38996; strains of the species *Stachybotrys chartarum* including, in particular, *Stachybotrys chartarum* MUCL 38898; *S. parvispora* MUCL 9485; *S. chartarum* MUCL 30782; *S. kampalensis* MUCL 39090; *S. theobromae* MUCL 39293; and strains of the species *S. bisbyi, S. cylindrospora, S. dichroa, S. oenanthes* and *S. nilagerica.*

Laccases (benzenediol:oxygen oxidoreductases; E.C. 1.10.3.2) are copper-containing enzymes that catalyze the oxidation of phenolics. Laccase-mediated oxidations produce aryloxy-radical intermediates from a phenolic substrate which result in the formation of dimeric to polymeric reaction products. In an embodiment, the enzyme composition of the invention comprises a laccase of a *Stachbotrys* species as disclosed in U.S. Pat. No. 6,426,410 (see also U.S. Pat. Nos. 6,168,936 and 6,905,853). In another embodiment, the enzyme composition of the invention comprises a laccase of *Trichoderma piluliferum.*

Laccase activity can be determined by any methods known in the art, such as syringaldazine oxidation monitored at 530 nm, 10-(2-hydroxyethyl)-phenoxazine (HEPO) oxidation which can be monitored photometrically at 528 nm, or oxidation of 2,2'-azinobis-(3-ethybenzthiazoline-6-sulfonic acid) (ABTS). For example, 60 µl of syringaldazine stock solution (0.28 mM in 50% ethanol) and 20 µl of laccase sample are mixed with 0.8 ml of preheated Britton-Robinson buffer solution and incubated at 20° C. The oxidation is monitored at 530 nm over 5 minutes and activity is expressed as "SOU" µmole syringaldazine oxidized per minute ("SOU"). See, Childs et al. (1975, Biochemical Journal 145: 93-103) and Bauer et al. (1971, Analytical Chemistry 43: 421-425).

In one embodiment, the phenol oxidizing enzyme(s) of the invention can be readily produced by synthetic techniques well known in the art if the amino acid sequence of the enzyme is known.

In another embodiment, phenol oxidizing enzymes of the present invention may be produced by cultivation of phenol oxidizing enzyme-producing organisms, including fungi, bacteria, and plants. Preferably, during cultivation, the phenol oxidizing enzyme-producing organism secretes the phenol oxidizing enzymes extracellularly. This permits the recovery, isolation and purification of the phenol oxidizing enzyme by, for example, separation of cell mass from a culture broth (e.g. by filtration or centrifugation). The resulting cell-free culture broth can be used as such or, if desired, may first be concentrated (e.g. by evaporation or ultrafiltration). If desired, the phenol oxidizing enzyme can then be separated from the cell-free broth and isolated to the desired degree of purity by conventional methods, e.g. by column chromatography, or even crystallized.

In a specific embodiment, the phenol oxidizing enzyme-producing organism is a recombinant organism comprising heterologous genetic materials that facilitate expression of a gene encoding the phenol oxidizing enzyme and/or production of the phenol oxidizing enzyme. The heterologous genetic material comprises a polynucleotide encoding an amino acid sequence that exhibits phenol oxidizing activities. The term "heterologous" when used with reference to portions of a nucleic acid indicates that the nucleic acid comprises two or more subsequences that are not normally found in the same relationship to each other in nature.

"Functionally equivalent," as the term is used herein, refers to a polypeptide capable of exhibiting a substantially similar phenol oxidizing activity or at least one chemical characteristics as the laccase from *Trichoderma piluliferum* as exemplified in Section 7 or the laccase from *Stachybotrys* species as described in U.S. Pat. No. 6,426,410 (see also U.S. Pat. Nos. 6,168,936 and 6,905,853). As used herein, the term "chemical characteristic" refers to the substrate or chemical functionality upon which the enzyme acts and/or the catalytic reaction performed by the enzyme.

In addition to the exemplified laccase DNA and proteins taught herein, the present invention contemplates the utilization of homologous or substantially identical phenol oxidizing enzymes. The term "identical" in the context of two polypeptide or nucleic acid sequences refers to the residues in the two sequences that are the same when aligned for maximum correspondence, as measured using one of the following "sequence comparison algorithms." Optimal alignment of sequences for comparison can be conducted, e.g., by the local homology algorithm of Smith & Waterman, Adv. Appi. Math. 2:482 (1981), by the homology alignment algorithm of Needleman & Wunsch, J. Mol. Biol. 48:443 (1970), by the search for similarity method of Pearson & Lipman, Proc. Nat'l Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. Another indication that two phenol oxidizing enzymes are substantially similar is that the first enzyme is immunologically cross-reactive with the second enzyme. Typically, enzymes that differ by conservative amino acid substitutions are immunologically cross-reactive. Thus, a phenol oxidizing enzyme is substantially similar to a second phenol oxidizing enzyme, for example, where the two enzymes differ only by a conservative substitution.

In addition, the methods of the invention also encompass proteins and polypeptides that are functionally equivalents of naturally occurring phenol oxidizing enzymes. Such equivalent phenol oxidizing enzymes can contain, e.g., deletions, additions or substitutions of amino acid residues within the amino acid sequences of known phenol oxidizing enzymes. Amino acid substitutions can be made on the basis of similarity in polarity, charge, solubility, hydrophobicity, hydrophilicity and/or the amphipathic nature of the residues involved. For example, nonpolar (i.e., hydrophobic) amino acid residues can include alanine (Ala or A), leucine (Leu or L), isoleucine (Ile or I), valine (Val or V), proline (Pro or P), phenylalanine (Phe or F), tryptophan (Trp or W) and methionine (Met or M); polar neutral amino acid residues can include glycine (Gly or G), serine (Ser or S), threonine (Thr or T), cysteine (Cys or C), tyrosine (Tyr or Y), asparagine (Asn or N) and glutamine (Gln or Q); positively charged (i.e., basic) amino acid residues can include arginine (Arg or R), lysine (Lys or K) and histidine (H is or H); and negatively charged (i.e., acidic) amino acid residues can include aspartic acid (Asp or D) and glutamic acid (Glu or E).

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, Science 244:1081-1085).

Functionally equivalent polypeptides corresponding to one or more domains of the enzyme gene products (e.g., signal sequences, active sites, or substrate-binding domains), truncated or deleted enzymes (e.g., polypeptides in which one or more domains of an enzyme are deleted) and fusion enzymes (e.g., proteins in which a full length or truncated or deleted enzyme, or a peptide or polypeptide corresponding to one or more domains of an enzyme is fused to an unrelated protein) are also within the scope of the present invention. Such functionally equivalent peptides and polypeptides (also referred to as chimeric protein or polypeptides) can be readily designed by those skilled in the art on the basis of the enzyme gene nucleotide and amino acid sequences. Exemplary fusion proteins can include, but are not limited to, epitope tag-fusion proteins which facilitate isolation of the enzyme gene product by affinity chromatography using reagents that binds the epitope. Other exemplary fusion proteins include fusions to any amino acid sequence that allows, e.g., the fusion protein to be immobilized onto a solid phase, thereby allowing the enzyme to be retained and re-used after a reaction. Accordingly, the invention provides a fusion protein comprising a fragment of a phenol oxidizing enzyme fused to a second polypeptide. Other modifications of the phenol oxidizing enzyme described above can be made to generate functionally equivalent polypeptides that are better suited, e.g., for scale up, for the pH environment of a particular lignocelluose biomass, etc. Accordingly, the present invention encompasses use of polypeptides that are functionally equivalent to phenol oxidizing enzymes.

The invention encompasses enzyme compositions comprising a catalytically effective amount of at least one phenol oxidizing enzyme, isolated, purified or enriched to various degrees, e.g., one of the phenol oxidizing enzyme can constitute about 0.1%, 0.25%, 0.5%, 0.75%, 1%, 2%, 5%, 10%, 20%, 40%, 50%, 75%, 80%, 90%, 95%, 99% of the total protein in the composition. Procedures for determining laccase activity, for example, are known in the art and include, e.g., the oxidation of the substrate 2,2'-azinobis-(3-ethybenzthiazoline-6-sulfonic acid ("ABTS") (see, Childs et al., 1975, Biochemical Journal 145:93-103) or syringaldazine (see, Bauer et al., 1971, Analytical Chemistry 43: 421-425), or the use of 2,6 dimethoxyphenol (see Haars et al., 1981, *European Journal of Forest Pathology*, 11 (1-2), 67-76.) or guaiacol (see Setti et al., 1999, *Enzyme and Microbial Technology*, 25(3-5), 285-289.)

The enzyme(s) in the composition are in a form suitable for use with the intended lignocellulose biomass, and may contain additional enzymes, stabilizing agents, preservatives, protease inhibitors, detergents, antifoaming agents, etc. Often these processes are cost-effective only when the enzymes can be re-used many times. For reuse of the enzymes, the enzymes need to be separated from the bulk of the process. This can be achieved when the enzymes are attached to a carrier or solid phase which can be isolated, for example by draining, filtration or centrifugation. This can also be achieved if the substrate is flowed across the surface of the solid phase where contacts with the enzymes are made. Accordingly, the present invention encompasses use of phenol oxidizing enzymes which exist not only in free-flowing soluble form, but also in immobilized or solid forms.

In another embodiment, the phenol oxidizing enzymes of the invention are immobilized in the form of proteins purified to varying degrees as described above. Any known method for immobilization of enzyme based on chemical and physical binding of the enzyme to a solid phase, e.g. polysaccharides, glass, synthetic polymers, magnetic particles, which are usually modified with functional groups, such as amine, carboxy, epoxy, phenyl or alkane to enable covalent coupling to amino acid side chains on the enzyme surface, can be used. The solid phase can be porous, with pore diameters in the range of 30 to 300 nm. Ionic and non-ionic adsorption to porous support can be a simple and effective method of immobilization. The enzymes can also be entrapped or encapsulated in polymeric gels, membranes, or micelles in surfactant-stabilized aqueous droplets. The choice of a suitable immobilization method for a given enzyme depends on enzyme characteristics, process demands, properties of support, and safety issues, and can be determined by one of skill in the art. Methods for immobilization of enzymes can be found, for example, in *Methods of Enzymology*, vol. 44, 135, 136, and 137, Academic Press, New York. Accordingly, the invention encompasses using an enzyme composition which comprises one or more solid phase(s), wherein catalytically active phenol oxidizing enzyme(s) are present on the solid phase(s).

The invention further encompasses using phenol oxidizing enzymes in solid form. Methods of making solid forms of enzymes are well known in the art, such as but not limited to prilling (spray-cooling in a waxy material), extrusion, agglomeration, or granulation (dilution with an inert material and binders). Solid enzyme compositions comprising a solid form of a phenol oxidizing enzymes, in the form of mixed powder, tablets, and the like, is contemplated

6.3 Production Microorganisms

According to the invention, lignocellulose biomass or a composition comprising lignocellulose biomass conditioned by phenol oxidizing enzymes can be used as a nutrient source for a variety of biotechnological processes. The conditioning of the lignocellulose biomass improves the growth rate of production microorganisms, accelerating the conversion of plant biomass to microbial biomass. Besides accumulating microbial biomass, in other embodiments, the objective of growing the microorganisms in lignocellulose biomass is to obtain one or more product(s) made by the microorganisms.

As a result of using the enzyme composition of the invention, in certain embodiments, not only the kinetics of the process is improved but the yield of the desired product(s) is also increased. The term "production microorganism" as used herein refers to a species of a microorganism which produces a desired product in a microbial process, or that is itself the desired product of a microbial process. The term also encompasses any progeny of the microorganisms growing in the process.

Many microbial processes that use lignocellulose biomass as a nutrient source can be benefited by the methods of the invention including but not limited to microbial processes for making industrially-useful enzymes, such as but not limited to a hydrolase, an oxidoreductase, an isomerase, a ligase, a lyase, or a transferase. More preferably, the enzyme is cellulases (endoglucnases, exoglucanses and β-glucosidases), tannases, oxidases, e.g., glucose oxidases, glucoamylases, phytases, β-galactosidases, sucrases or invertases, lipases, proteases, amylases, laccases, polygalacturonases, carboxypeptidases, catalases, chitinases, cutinases, cyclodextrin glycosyl transferases, deoxyribonucleases, esterases, haloperoxidases, laccases, mannosidases, pectinolytic enzymes, peroxidases, xylose isomerases and xylanases. Other useful products that are produced by microbial cultures include organic acids, such as but not limited to citric acid, itaconic acid, gluconic acid, fumaric acid, malic acid, lactic acid, and tartaric acid; amino acids, such as but not limited to, tryptopham, lysine, methionine, glutamic acid, threonine, alanine, phenylalanine, and aspartic acid; polysaccharides such as but not limited to pullulan; lipids, nucleotides, and vitamins. Other useful products that are produced by microbial cultures include alcohols, such as but not limited to, ethanol. Other useful products that are produced by microbial cultures include glucose which can subsequently used by another microorganism to make ethanol, or used as a fermentation substrate to make any kind of microbial based product.

Production microorganisms include but are not limited to bacteria and fungi, including yeasts. Many Ascomycetes, Basidiomycetes, and Deuteromycetes are known for their cellulolytic enzymes and/or wood-degrading capability and can use lignocellulose biomass as a nutrient source. Such fungi include but is not limited to species within the genera *Bulgaria, Chaetomium* and *Helotium* (Ascomycetes); *Coriolus, Phanerochaete, Poria, Schizophyllum* and *Serpula* (Basidiomycetes); and *Aspergillus, Cladosporium, Fusarium, Geotrichum, Myrothecium, Paecilomyces, Penicillium* and *Trichoderma* (Deuteromycetes). Exemplary species that can use lignocellulose biomass as a nutrient include but are not limited to *Trichoderma* or *Hypocrea* species. In one embodiment, the *Trichoderma* species is *Trichoderma reesei*.

Several diverse groups of bacteria can grow on lignocellulose biomass: (i) fermentative anaerobes, typically gram positive (*Clostridium, Ruminococcus*, and *Caldicellulosiruptor*) but containing a few gram-negative species, (*Butyrivibrio* and *Acetivibrio, Fibrobacter*); (ii) aerobic gram-positive bacteria (*Cellulomonas* and *Thermobifida*); and (iii) aerobic gliding bacteria (*Cytophaga* and *Sporocytophaga*). Exemplary bacteria that can use lignocellulose as a nutrient include but are not limited to *Clostridium thermocellum, Clostridium cellulolyticum, Clostridium cellulovorans* and *Clostridium josui*.

Development of microorganisms for cellulose conversion are pursued according to two strategies. The native cellulolytic strategy involves naturally occurring cellulolytic microorganisms to improve product-related properties such as yield and tolerance. Such microorganisms can be production microorganisms of the invention and include but are not limited to *Clostridium thermocellum, Neurospora crassa,*

*Trichoderma viride, Zygosaccharomyces* species, *Aspergillus* species and *Paecilomyces* species. The recombinant cellulolytic approach involves engineering noncellulolytic microorganisms that exhibit high product yields and tolerance so that they become able to utilize cellulose as a result of a heterologous cellulase system. Such microorganisms can also be production microorganisms of the invention and include but are not limited to *Saccharomyces cerevisiae, Escherichia coli*, and *Zymomonas mobilis*. Accordingly, the methods of the invention can be used to improve the growth kinetics and/or yield of culture of microorganisms that naturally express cellulases or that are genetically engineered to express heterologous cellulase(s), and that enable their use of cellulose as a nutrient source.

6.4 Methods of the Invention

The present invention provides a method for treating a lignocellulose biomass or a composition comprising lignocellulose biomass (such as a feedstock comprising other nutrients) with an enzyme composition comprising a phenol oxidizing enzyme, such that the growth rate of a production microorganism on said lignocellulose biomass or said composition is increased relative to lignocellulose biomass or composition comprising lignocellulose biomass that has not been treated with the enzyme composition. The increase in growth rate of a production microorganism in a process can be estimated by a number of parameters, such as, but not limited to, nutrient consumption, catabolite accumulation, pH, cell mass, cell number, etc. In various embodiments of the invention, the treatment with the enzyme composition increases the initial growth rate of the microorganisms in a culture where a composition comprising lignocellulose biomass is used as a nutrient source.

In one embodiment, the invention provides a method for conditioning lignocellulose biomass or a composition comprising lignocellulose biomass. The method involves contacting an enzyme composition comprising a phenol oxidizing enzyme with the lignocellulose biomass or the composition comprising lignocellulose biomass. The term "contacting" is used herein interchangeably with the following: introducing into, combined with, added to, mixed with, passed over, incubated with, injected into, flowed over, etc. It is contemplated that different forms of the phenol oxidizing enzyme as described above can be used. The conditioning or treatment process can occur over a period of time, ranging from 1 hour, 2, 5, 10, 15, 24, 36, 48, 60, 72 hours, to 4, 5, 6, 7 days, or until the inhibitory activity of the lignocellulose biomass is reduced to an acceptable level, e.g., less than 1%, 2%, 5%, 10%, 25%, 30%, 40%, 50%, 60% 70%, 80%, 90%, 95% of the original level. The time period for contact can also be determined by measuring the increase in growth rate of a microorganism that is supported by the conditioned composition, e.g., at least 110%, 120%, 125%, 130%, 140%, 150%, 175%, 200%, 300, 400%, 500% or 1000% of the original rate.

Preferably, the contacting step is carried out under a temperature within a range that the enzyme exhibits substantial or optimal activity. Preferably, the contacting step is carried out in a pH range where the enzyme exhibits substantial or optimal activity. Accordingly, the invention encompasses a composition comprising a lignocellulose biomass which has been treated or conditioned to support microbial growth with an enzyme composition comprising a phenol oxidizing enzyme. Such a composition can be used as a feedstock or used as a component to make a feedstock. The conditioned lignocellulose biomass can be used as a feedstock for a variety of microbial process. In certain embodiments, the lignocellulose biomass is the sole nutrient source or sole carbon source in the composition. In one embodiment, the invention provides a method for making a feedstock comprising contacting an enzyme composition comprising a phenol oxidizing enzyme with the lignocellulose biomass or the composition comprising lignocellulose biomass, and adding other nutrients and/or feedstock components to the conditioned lignocellulose biomass. In some embodiments, the enzyme composition is removed from the composition comprising the lignocellulose biomass prior to the use of the composition in a microbial process. In various embodiments, a range of enzyme concentrations can be used to condition the feedstock, e.g., from about 0.0001 g/l to about 100 g/l, such as but not limited to 0.001 g/l, 0.1 g/l, 1 g/l, 10 g/l. In various embodiments, a range of duration of the treatment or conditioning can be used, e.g., about 15 seconds to about 200 hours, such as but not limited to 1 minute, 5 minutes, 15 minutes, 30 minutes, 45 minutes, 1 hour, 2 hours, 5 hours, 10 hours, 24 hours, 36 hours, 72 hours, or 96 hours. In various embodiments, the treatment or conditioning can be carried out in a range of temperatures, e.g., at about 15° C. to about 100° C., such as but not limited to, 20° C., 25° C., 30° C., 35° C., 40° C., 50° C., 60° C., 70° C., 80° C., 90° C., or ambient temperature at the place of treatment or conditioning. In various embodiments, the treatment or conditioning can be carried out in a range of pH, e.g., in about pH 2 to about pH 10, such as but not limited to about pH3, pH4, pH5, pH6, pH7, pH8, or pH9. In one embodiment the methods are carried out in the range of pH 4.5 to 6.5. In another embodiment the pH is about 4.5 to 5.5.

The invention further provides methods for culturing production microorganisms in a culture medium comprising lignocellulose biomass, wherein the methods comprise contacting the culture medium with an enzyme composition comprising a phenol oxidizing enzyme. In another embodiment, the invention provides the use of conditioned lignocellulose biomass to grow microorganisms. The invention further provides methods for producing a product where the product is made by a production microorganism that is cultured in a culture medium comprising conditioned lignocellulose biomass. Such methods comprise growing the production microorganisms in a culture medium treated with an enzyme composition comprising a phenol oxidizing enzyme and recovering the product from the culture and/or the microorganisms.

It is contemplated that microbial processes for production of a desired product include solid or submerged culture, including batch, fed-batch and continuous-flow processes. Culturing is accomplished in a medium which comprise an aqueous mineral salts medium, organic growth factors, carbon source materials, energy source materials, or a combination thereof, and a starting inoculum of one or more production microorganism species to be employed.

It is contemplated that the invention can be applied to many different types of processes as well as different stages of a complex process. An example of a complex process is converting lignocellulose to sugars and then to ethanol, which may involve different microorganisms at distinct stages of the process.

In the context of converting lignocellulose into fuels and chemicals, the following processes are involved: (i) cellulase production, (ii) hydrolysis of cellulose and if present other insoluble polysaccharides (saccharification), (iii) fermentation of soluble cellulose hydrolysis products, and (iv) fermentation of soluble hemicellulose hydrolysis products. To the extent that these processes are carried out by growing microorganisms in the presence of lignocellulose biomass, the enzyme composition or conditioned lignocelluose biomass of the invention can be used in one or more of these individual steps to improve the growth kinetics of the microorganisms and/or the yield of each step.

These four steps can be carried out separately or consolidated in various configurations. Simultaneous saccharification and fermentation (SSF) consolidates hydrolysis and fermentation of cellulose hydrolysis products into one process step, with cellulase production and fermentation of hemicellulose hydrolysis products occurring in two additional discrete process steps. Simultaneous saccharification and cofermentation (SSCF) involves two process steps: cellulase production and a second step in which cellulose hydrolysis and fermentation of both cellulose and hemicellulose hydrolysis products occur. In consolidated bioprocessing (CBP), cellulase production, hydrolysis, and fermentation of products of cellulose and hemicellulose are combined. According to the invention, the enzyme composition can also be used in one or more steps in these consolidated processes to improve the growth kinetics of the microorganisms and/or the yield of each step. Alternatively, conditioned lignocellulose biomass (previously treated with the enzyme composition of the invention) can be used in one or more steps in these consolidated processes.

Accordingly, in one embodiment of the invention, an enzyme composition comprising one or more phenol oxidizing enzyme(s) can be used in a process of making cellulases. The enzyme composition can be added to the culture of production microorganisms that makes cellulase that comprises lignocellulose biomass as a nutrient source. The method may also encompass recovering the cellulases from the culture.

In another embodiment, an enzyme composition comprising one or more phenol oxidizing enzyme(s) can be used in a process of growing microorganisms in a culture medium comprising lignocellulose biomass, wherein the microorganism hydrolyses cellulose and other insoluble polysaccharides to form disaccharides and monosaccharides. The process may optionally include recovering the disaccharides and monosaccharides.

In yet another embodiment, an enzyme composition comprising one or more phenol oxidizing enzyme(s) can be used in a process of growing microorganisms in a culture medium comprising lignocellulose biomass, wherein the microorganisms are capable of converting sugars (such as disaccharides and monosaccharides) to ethanol or other low molecular weight chemicals, such as acetic acid or lactic acid. In yet another embodiment, an enzyme composition comprising one or more phenol oxidizing enzyme(s) can be used in a process of growing microorganisms that are capable of converting hemicellulose to ethanol or other low molecular weight chemicals, such as acetic acid or lactic acid.

In each of the above embodiments, instead of using the enzyme composition directly in the process, it can be used to treat a composition comprising lignocellulose biomass which is then used for culturing the production microorganisms.

In various embodiments, the lignocellulose biomass used in any of the abovementioned processes is lignocellulose derived from a woody plant, lignocellulose derived from a non-woody plant, a hydrolysate of a lignocellulose, or a mixture of a lignocellulose and its hydrolysate.

In certain embodiments of the invention, the lignocellulose biomass used in a process of fermentation to make ethanol is not woody lignocellulose biomass, such as wood hydrolysates. In other embodiments of the invention, the lignocellulose biomass used in the process is not hemicellulose hydrolysates. In certain embodiments, the production microorganisms that can grow on woody lignocellulose biomass and make ethanol are not strains of *Saccharomyces cerevisiae*. In certain embodiments, the enzyme composition used in the process does not comprise a laccase derived from a basidiomycete, such as a laccase of *Trametes versicolor*.

In an embodiment of the invention, the enzyme composition is used in a simultaneous saccharification and fermentation process. In yet another embodiment, the enzyme composition is used in a simultaneous saccharification and cofermentation process. In yet another embodiment, the enzyme composition is used in consolidated bioprocessing. In one embodiment, the concentration of enzyme used for treating lignocellulose biomass ranges from about 0.001 g/l to 100 g/l. In a related embodiment, the concentration of the enzyme used for treating lignocellulose biomass is not less than about 60 g/l, about 30 g/l, about 1 g/l, about 0.6 g/l, about 0.3 g/l, about 0.01 g/l, about 0.006 g/l, or about 0.003 g/l.

7. EXAMPLES

The present invention may be better understood by reference to the following non-limiting example, which is provided only as exemplary of the invention. The following examples are presented to more fully illustrate an embodiment of the invention. The examples should in no way be construed, however, as limiting the broader scope of the invention.

The experiment was conducted with *Trichoderma piluliferum* laccase, raw corn stover as the lignocellulose biomass, and *Trichoderma reesei* as the production microorganism.

7.1 Materials and Methods

*Trichoderma reesei* Enzyme Production

An inoculum of *Trichoderma reesei* RL-P37 (see Sheir-Neiss et al. in *Appl. Microbiol. Biotechnology*, 20 (1984) pp. 46-53) was prepared as follows: a shake flask containing $(NH_4)_2SO_4$ (4 g), $KH_2PO_4$ (4.5 g), $MgSO_4.7H_2O$ (1 g), $CaCl_2.2H_2O$ (1 g), NaCl (0.01 g), Mazu DF 204 5 drops/L (0.2 ml), pH 5.5, q.s. to 897.5 mls. After sterilization, 100 ml of 50% glucose and 2.5 ml of *T. reesei* trace elements solution was added. *T. reesei* trace element solution contained per litre: citric acid (anhydrous) 175 g, $FeSO_4.7H_2O$ (200 g), $ZnSO_4.7H_2O$ (16 g), $CuSO_4.5H_2O$ (3.2 g), $MnSO_4.H_2O$ (1.4 g), $H_3BO_3$ (Boric Acid) (0.8 g). Glucose was the sole carbon source at a concentration of 10 g/L. The culture was inoculated with about one million spores of RLP-37 per 50 ml in a 250 ml flask. The flask was incubated at 26-28° C., 150 rpm, for 3-5 days until good growth was obtained. Growth of the culture can be followed by measuring the pH and glucose concentration over time by standard techniques. Before exhaustion of glucose, fungal cells can be taken to inoculate flasks for the experiment.

In this experiment, two sets of flasks were set up, each flask containing the same media as above and 2% raw corn stover. The lignocellulose-containing corn materials had been shredded, washed with water to remove soil and other farm debris, then air dried. The appearance was that of dry grass clippings. It was added to the culture flasks in this dry form and the flasks were autoclaved to sterilize the contents before the culture was introduced. To a set of flasks was added an aliquot of a filtrate containing laccase from a culture of *Trichoderma piluliferum*. Three different concentrations of laccase, namely 0.125 U/ml, 0.25 U/ml and 0.5 U/ml, were used.

The presence of phenol oxidizing enzyme activity in the supernatant was measured using the following assay procedure, based on the oxidation of ABTS (2,2'-azino-bis-(3- ethylbenzothiazoline-6-sulfonate)) by oxygen. ABTS (SIGMA, 0.2 ml, 4.5 mM $H_2O$) and NaOAc (1.5 ml, 120 mM in $H_2O$, pH 5.0) were mixed in a cuvette. The reaction was started by addition of an appropriate amount of the preparation to be measured (which in this example is the supernatant dilution) to form a final solution of 1.8 ml. The color produced by the oxidation of ABTS was then measured every 2 seconds for total period of 14 seconds by recording the optical density (OD) at 420 nm, using a spectrophotometer. One ABTS unit (one enzyme unit or EACU) in this example is defined as the change in OD measured at 420 per minute (given no dilution to the sample).

The control set of flasks lack the laccase. The flasks were incubated for one, two or three days at 30° C. before being inoculated with about one million RLP-37 cells that had been grown for 24 hours as described above. The two sets of flasks containing the RLP-37 cells were grown shaking at 100-250 rpm at 20-28° C. for up to 72 hours. The growth of *T. reesei* in the two sets of cultures was monitored by measuring the glucose concentration in the culture media which drops gradually as the growing fungi consume glucose.

7.2 Results

The results of the experiment are shown in FIG. 1. Decreasing glucose concentration indicates good growth of the fungal cells. The best growth rates were obtained in flasks containing a culture medium comprising a lignocellulose biomass (2% corn stover) that had been conditioned by 0.5 U/ml laccase for at least two days. In two flasks (2 and 3 days of conditioning with 0.5 U/ml), all the glucose in the flasks were exhausted by the third day of *T. reesei* culturing. Lower laccase doses or shorter conditioning periods produced cultures with less rapid growth. Less than 50% of the glucose was consumed by the fungi in flasks that were treated with 0.25 U/ml or 0.125 U/ml laccase irrespective of the period of conditioning. The control flask that had not been treated with laccase showed the slowest growth.

8. EQUIVALENTS

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

What is claimed is:

1. A method for culturing a production microorganism that produces a desired product, which is an enzyme, said method comprising:
   contacting a composition comprising a lignocellulose biomass with a cell-free composition comprising a phenol oxidizing enzyme for a period of time sufficient to condition said composition for microbial growth, and
   growing said production microorganism in said conditioned composition,
   wherein said lignocellulose biomass has not been subjected to a chemical pretreatment with acid, said phenol oxidizing enzyme is a laccase from *Trichoderma piluliferum*, and said production microorganism is *Trichoderma reesei*,
   wherein the rate of growth of said production microorganisms cultured in said conditioned composition is increased relative to that of a composition comprising lignocellulose biomass that was not contacted with said phenol oxidizing enzyme.

2. The method of claim 1, wherein said lignocellulose biomass has not been subjected to alkali pretreatment.

3. The method of claim 1, wherein said lignocellulose biomass comprises hydrolysates of lignocellulose biomass.

4. The method of claim 1, wherein said lignocellulose biomass comprises non-woody lignocellulose biomass.

5. The method of claim 4, wherein said non-woody lignocellulose biomass is corn stover or sugarcane bagasse.

6. The method of claim 1, wherein said product, which is an enzyme is a cellulase.

7. The method of claim 4, wherein said non-woody lignocellulose biomass is corn stover.

8. The method of claim 1, wherein said cell-free composition is a culture broth.

* * * * *